(12) United States Patent
Petit

(10) Patent No.: US 7,717,941 B2
(45) Date of Patent: May 18, 2010

(54) LINKING ELEMENT FOR DYNAMICALLY STABILIZING A SPINAL FIXING SYSTEM AND SPINAL FIXING SYSTEM COMPRISING SAME

(75) Inventor: Dominique Petit, Verton (FR)

(73) Assignee: Spinevision, Paris (FR)

( * ) Notice: Subject to any disclaimer, the term of this patent is extended or adjusted under 35 U.S.C. 154(b) by 0 days.

(21) Appl. No.: 10/527,490

(22) PCT Filed: Sep. 11, 2003

(86) PCT No.: PCT/FR03/02695
§ 371 (c)(1), (2), (4) Date: Nov. 17, 2005

(87) PCT Pub. No.: WO2004/024011
PCT Pub. Date: Mar. 25, 2004

(65) Prior Publication Data
US 2006/0142758 A1    Jun. 29, 2006

(30) Foreign Application Priority Data
Sep. 11, 2002   (FR) .................................. 02 11251

(51) Int. Cl.
*A61B 17/70*   (2006.01)
(52) U.S. Cl. ...................... 606/257; 606/254
(58) Field of Classification Search ............... 606/61, 606/72, 73
See application file for complete search history.

(56) References Cited

U.S. PATENT DOCUMENTS

| 1,938,099 | A | * | 12/1933 | Endsley | 267/135 |
|---|---|---|---|---|---|
| 2,103,946 | A | * | 12/1937 | Herr | 267/33 |
| 3,807,394 | A | * | 4/1974 | Attenborough | 606/60 |
| 4,697,582 | A | | 10/1987 | William | |
| 4,763,882 | A | * | 8/1988 | Nishiyama et al. | 267/33 |
| 4,886,256 | A | * | 12/1989 | Nishiyama et al. | 267/221 |
| 5,180,393 | A | * | 1/1993 | Commarmond | 623/13.14 |
| 5,672,175 | A | | 9/1997 | Martin | |
| 6,402,750 | B1 | * | 6/2002 | Atkinson et al. | 606/279 |
| 6,986,771 | B2 | * | 1/2006 | Paul et al. | 606/61 |
| 2001/0012937 | A1 | * | 8/2001 | Schaffler-Wachter et al. | 606/61 |
| 2002/0173791 | A1 | * | 11/2002 | Howland | 606/61 |
| 2003/0220643 | A1 | * | 11/2003 | Ferree | 606/61 |
| 2004/0049190 | A1 | * | 3/2004 | Biedermann et al. | 606/61 |

FOREIGN PATENT DOCUMENTS

| EP | 0 516 567 | A1 | | 12/1992 |
|---|---|---|---|---|
| FR | 2 702 363 | A1 | | 9/1994 |
| FR | 2 717 370 | A1 | | 9/1995 |
| FR | 2 718 946 | A1 | | 10/1995 |
| GB | 2382304 | A | * | 5/2003 |

* cited by examiner

*Primary Examiner*—Thomas C Barrett
*Assistant Examiner*—Nicholas Woodall
(74) *Attorney, Agent, or Firm*—Bachman & LaPointe, P.C.

(57) ABSTRACT

A linking element for a spinal fixing system is designed to link at least two implantable connecting assemblies. The linking element is formed at least partly of a support made of polymeric material and of two rods with a first rod, bent or not, substantially coaxial with the support, and a second rod formed of turns surrounding the first rod with the turns being at least partly embedded in the support. A spinal fixing system has at least two implantable connecting assemblies linked by at least one linking element.

15 Claims, 16 Drawing Sheets

A-A

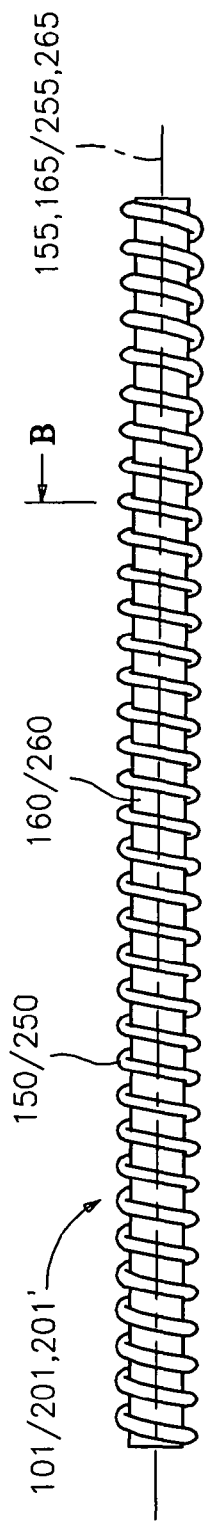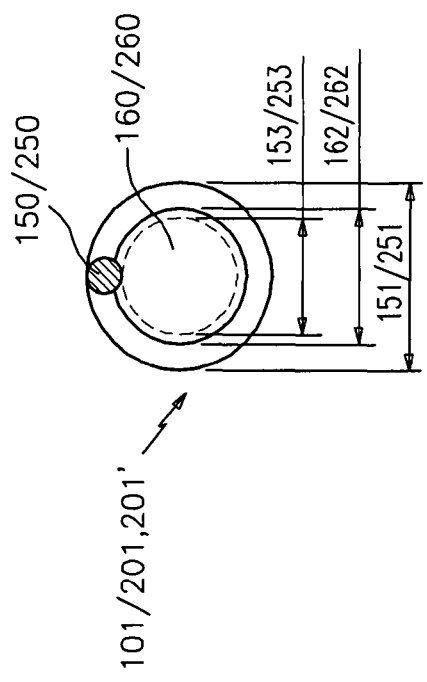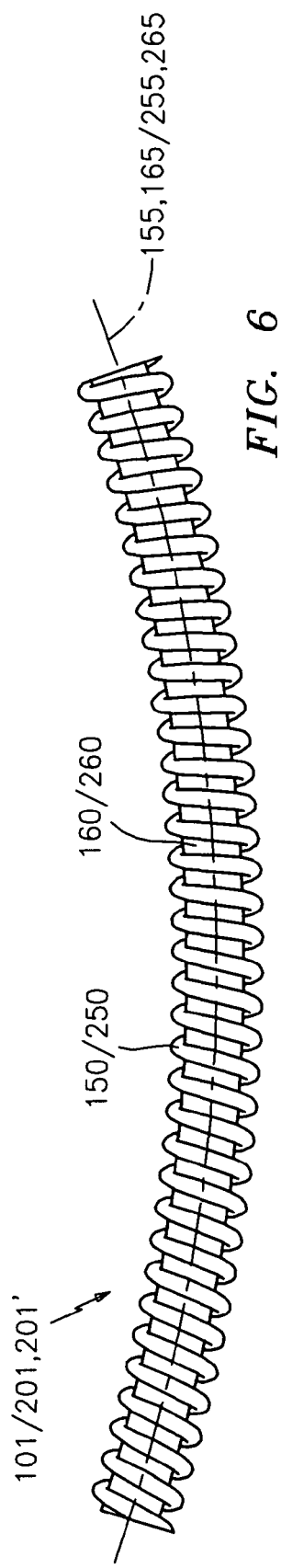

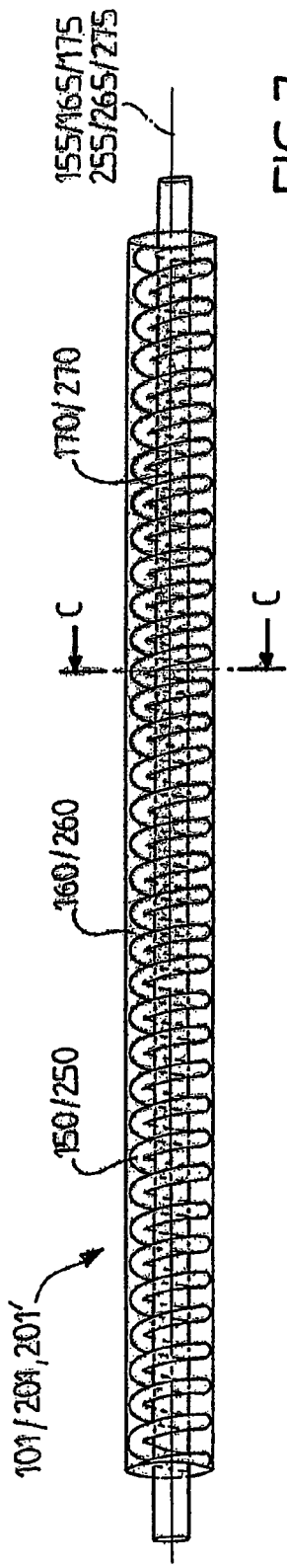
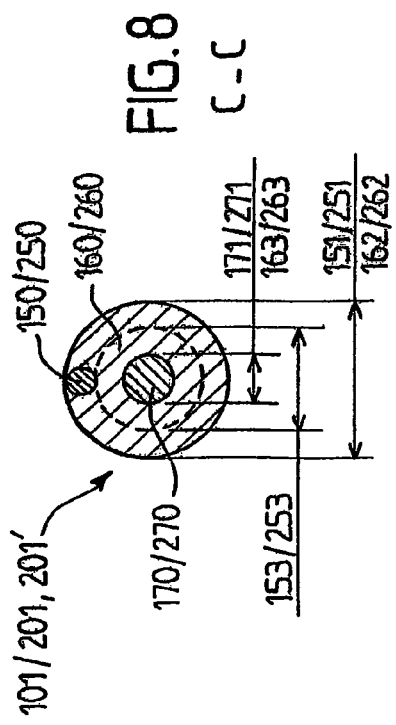
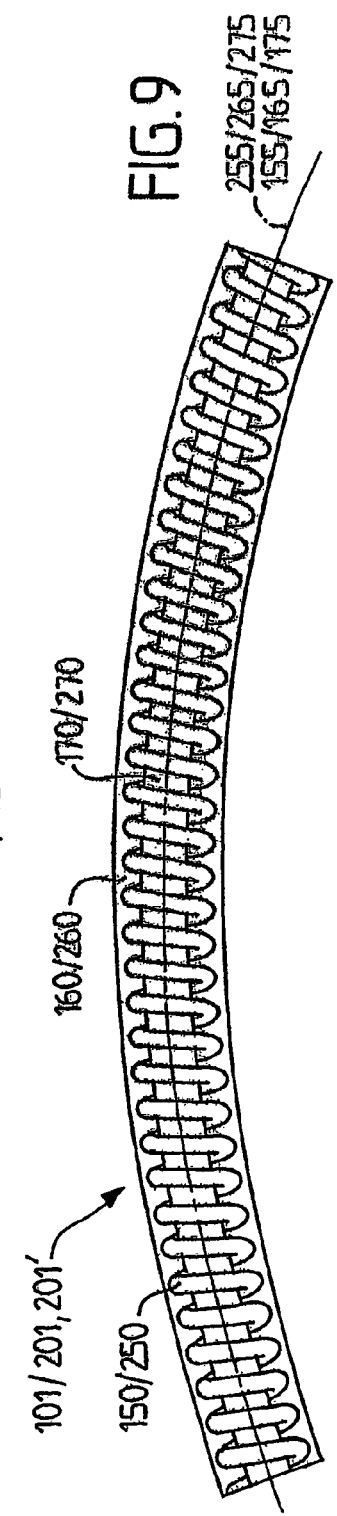

LINKING ELEMENT FOR DYNAMICALLY STABILIZING A SPINAL FIXING SYSTEM AND SPINAL FIXING SYSTEM COMPRISING SAME

BACKGROUND OF THE INVENTION (1) Field of the Invention

The present invention relates to the field of spinal systems for linking the vertebrae.

(2) Prior Art

There are two types of spinal links: osteosynthesis links, and dynamic links.

Spinal osteosynthesis links have the aim of setting the linked vertebrae in a specific configuration and of stabilizing them during bone fusion in order to permit fixed stabilization in the set position.

Dynamic links, by contrast, do not generate bone fusion but instead seek to reduce the stresses on the articular facets and on the intervertebral disks, by permitting certain movements, while at the same time realigning the vertebrae relative to one another, if necessary.

The present invention relates more particularly to a linking and dynamically stabilizing element for a spinal fixation system, designed to link at least two implantable connecting assemblies to one another, permitting certain possibilities of movement of one relative to the other.

Linking elements for dynamic stabilization are already known from the prior art.

European patent application EP669109 proposes a device for stabilizing adjacent thoracic vertebrae, comprising a band which is made of an elastic synthetic material and which has a round cross section, and at least two pedicle screws. The band can be inserted through the transverse hole in the head of the screws and fixed by a locking screw transversely with respect to the hole, that is to say in the direction of the screw axis.

The device additionally comprises a bearing element mounted on the band. This bearing element forms a pressure-resistant body in order to transfer pressure forces between the two screw heads. The cross section of the band fits in suitable holes of the bearing element and of the screw head in order to center the bearing element and the screw head relative to one another.

In addition, the band can be pre-stressed between two adjacent pedicle screws by a band extension which protrudes outside the pedicle screws in order to be able to mutually support the bearing element and the screw head on a bearing surface which is common to them and is arranged around the band.

A major disadvantage of this stabilizing device is that the band has to be slid into the hole formed in the head of the pedicle screws, and also through the bearing element(s). This first entails a difficulty, upon implantation, in passing the band through these elements, as the pedicle screws are already fixed to the vertebrae. Introduction of the band is not easy; but it means above all that the length of the bearing element has to be chosen before the band is put in place. It may well happen that the effective distance between the screws after tensioning of the band is not exactly the distance desired, and in this case the surgeon has no other choice than to dismantle the assembly made up of bearing element and band in order to introduce a bearing element of a different length. In fact, this system does not afford any freedom in terms of compression or distraction between the screws after the elements have all been put in place. Moreover, the viscoelastic material of the bearing element compresses when the band is tensioned, which further complicates the choice of length of the bearing element since this changes during tensioning of the band.

Another major disadvantage of the stabilizing device of the prior art is that the linking element takes up a considerable volume: of the order of 12.5 millimeters. In some circumstances, it is then difficult to avoid the linking element coming into contact with bones and this contact causing great pain.

Another major disadvantage of the stabilizing device of the prior art is that the linking element does not effect any torsional return in order to oppose pivoting movements of the vertebrae about the disks.

Another major disadvantage of the stabilizing device of the prior art is that the linking element cannot be curved in order to adapt it to the natural curvature of the lumbar spine.

Another major disadvantage of the device is the impossibility of performing surgical revision to extend the assembly, or of replacing the linking element by a rigid rod in order to obtain osteosynthesis without complete removal of the material beforehand.

Another disadvantage of the device is the impossibility of combining it with a conventional osteosynthesis system.

SUMMARY OF THE INVENTION

The present invention aims to overcome the disadvantages of the prior art by proposing a linking element for a spinal fixation system which can be inserted into an implantable connecting assembly, on the head of this assembly, in a conventional manner, such as a linking rod for osteosynthesis which has a small diameter, which provides torsional return in order to incite a return to a position of equilibrium, which can be curved, which can be combined with an osteosynthesis system, and which can also be easily interchanged to perform osteosynthesis.

To do this, the present invention is of the type described above and it is distinguished, in its widest sense, by the fact that the linking element is composed, at least partly, of a support made of polymer material and of a rod, curved or not, substantially coaxial with said support.

Said support preferably has a substantially tubular or cylindrical shape.

Advantageously, said linking element additionally comprises a helical spring substantially coaxial with said support, said spring having turns which are at least partly embedded in said support.

Said rod preferably has an external diameter smaller than the internal diameter of said turns.

To perform osteosynthesis, the linking element preferably comprises a straight or curved stiffening element.

This stiffening element is preferably composed of a sheet of material with a substantially U-shaped cross section.

The present invention also relates to a spinal fixation system comprising at least two implantable connecting assemblies linked by at least one linking element according to the invention, said linking element being composed, at least partly, of a support made of polymer material and of a rod, curved or not, substantially coaxial with said support.

To perform osteosynthesis, when the fixation system comprises a stiffening element, this element is preferably fixed at least to the two implantable connecting assemblies.

To perform osteosynthesis, the fixation system may additionally comprise at least one rigid linking element.

Advantageously, the linking element according to the invention is easy to insert into the receiving means of an implantable connecting assembly of known type. The placement of the linking element according to the invention does not involve the use of an implant specifically designed for this. The implant technique is therefore the same as for fusion.

Advantageously too, the structure of the linking element according to the invention makes it possible to obtain the desired resistance to compression and extension while requiring only a small volume. In addition, as the external diameter of the linking element according to the invention is substantially the same as that of the linking elements used for fusion, it is possible, within the same fixation system, to provide a combination of transverse links for fusion and transverse links for dynamic stabilization.

Advantageously too, the structure of the linking element according to the invention also permits torsional return in order to force a return to a defined configuration of equilibrium.

Advantageously too, the structure of the linking element according to the invention allows it to be adapted to the implantation configuration by giving it the desired shape, and in particular by curving it in advance.

Advantageously too, the structure of the linking element according to the invention permits compression and distraction directly on the screws.

BRIEF DESCRIPTION OF THE DRAWINGS

The invention will be better understood from the following description, given solely by way of example, of an embodiment of the invention, with reference being made to the attached figures in which:

FIG. 4 shows a front view of a second embodiment of the linking element according to the invention, straight;

FIG. 5 shows a cross section along line AA in FIG. 4;

FIG. 6 shows a front view of a second embodiment of the linking element according to the invention, curved;

FIG. 7 shows a front view of a third embodiment of the linking element according to the invention, straight;

FIG. 8 shows a cross section along line AA in FIG. 7;

FIG. 9 shows a front view of a third embodiment of the linking element according to the invention, curved;

DETAILED DESCRIPTION OF THE PREFERRED EMBODIMENT(S)

Figure 1:
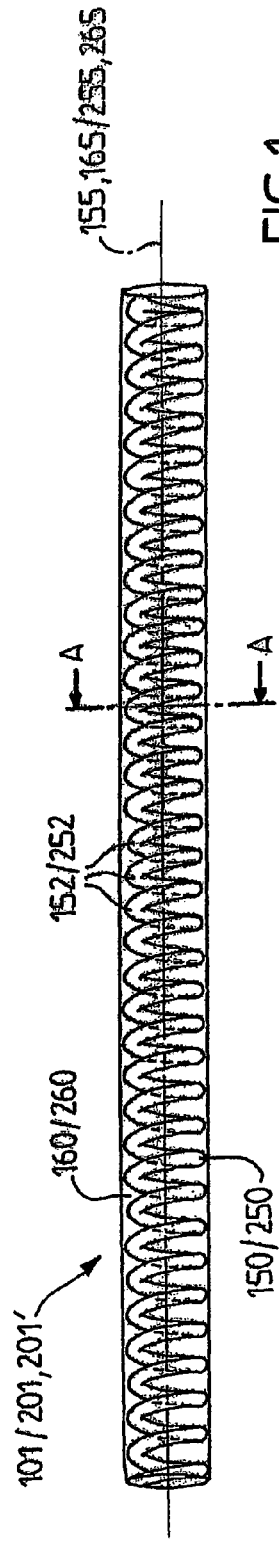
FIG. 1 shows a front view of a first embodiment of the linking element according to the invention, straight.

The linking element (101, 201, 201') for a spinal fixation system (100, 200) according to the invention is designed to link at least two connecting assemblies (102, 202) which are implantable in the spine with the aid of bone-anchoring means.

An implantable connecting assembly (102) according to the first embodiment of the invention is an assembly such as the one which is known from international patent application WO 01/01873 and whose cooperation with the linking element according to the present invention is described in greater detail below, with reference to FIGS. 10 through 19.

An implantable connecting assembly (202) according to the second embodiment of the invention is an assembly such as the one which is known from international patent application WO 01/39677 and whose cooperation with the linking element according to the present invention is described in greater detail below, with reference to FIGS. 20 through 23.

The linking element (101, 201, 201') is substantially tubular or cylindrical and has a longitudinal axis. Its external diameter is of the order of 6 millimeters.

The linking element (101, 201, 201') according to the invention is composed, at least partly, of:

on the one hand, a helical spring (150, 250) having an axis (155, 255) and turns (152, 252) and, on the other hand, a support (160, 260) made of polymer material and having an axis (165, 265) substantially parallel with the axis of said helical spring (150, 250).

Said turns are at least partly embedded in at least one support (160, 260) made of polymer material.

The helical spring (150, 250) can be made of metal, or of metal alloy, or of any type of biocompatible material permitting production of such a spring. It has turns (152, 252) with an external diameter (151, 251) and an internal diameter (153, 253). The diameter of the metal rod forming the turns is of the order of 0.8 millimeter for a titanium-based alloy material.

The support (160, 260) can be made, for example, of elastic biomaterial (polycarbonate, polyvinyl, alcohol, etc.). It is of a substantially tubular or cylindrical shape and has an external diameter (162, 262) and, if appropriate, an internal diameter (163, 263).

The external diameter (162, 262) of the support (160, 260) can be greater than the external diameter (151, 251) of the helical spring (150, 250), and the support (160, 260) can consequently completely enclose the helical spring (150, 250); however this external diameter (162, 262) cannot be smaller than the internal diameter (153, 253) of the helical spring (150, 250). In other words, in cross section, the turns (152, 252) are always at least partly enclosed in polymer material of the support (160, 260).

Although not illustrated here, it is also possible to imagine that the internal diameter (163, 263) of the support (160, 260) is greater than the internal diameter (153, 253) of the helical spring (150, 250).

In the linking elements (101, 201, 201') illustrated, the helical spring (150, 250) and the support (160, 260) have a substantially identical length; however, it is possible to imagine that at one or both ends the spring is shorter than the support, or vice versa.

Figure 2:
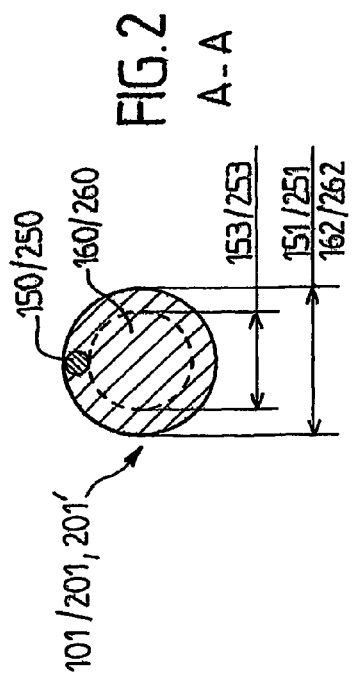
FIG. 2 shows a cross section along line AA in FIG. 1.

FIGS. 1 and 2 show a first embodiment of the linking element according to the invention, in which the support (160, 260) is cylindrical and has an external diameter (162, 262) substantially identical to the external diameter (151, 251) of the turns (152, 252).

FIGS. 4 and 5 show a second embodiment of the linking element according to the invention, in which the support (160, 260) is cylindrical and has an external diameter (162, 262) smaller than the external diameter (151, 251) of the turns (152, 252), but without being smaller than the internal diameter (153, 253) of the turns (152, 252).

FIGS. 7 and 8 show a third embodiment of the linking element according to the invention, in which the support (160, 260) is tubular and has an external diameter (162, 262) substantially identical to the external diameter (151, 251) of the turns (152, 252), and an internal diameter (163, 263) smaller than the internal diameter (153, 253) of the turns (152, 252). In addition, the linking element comprises a rod (170, 270) at its center. This rod (170, 270) has an axis (175, 275) substantially coaxial with the axis (155, 255) of said spring (150, 250).

This rod (170, 270) additionally has an external diameter (171, 271) smaller than the internal diameter (153, 253) of said turns (152, 252).

The rod (170, 270) can be made of metal, or of metal alloy, or of any type of material permitting production of such a rod.

Figure 3:
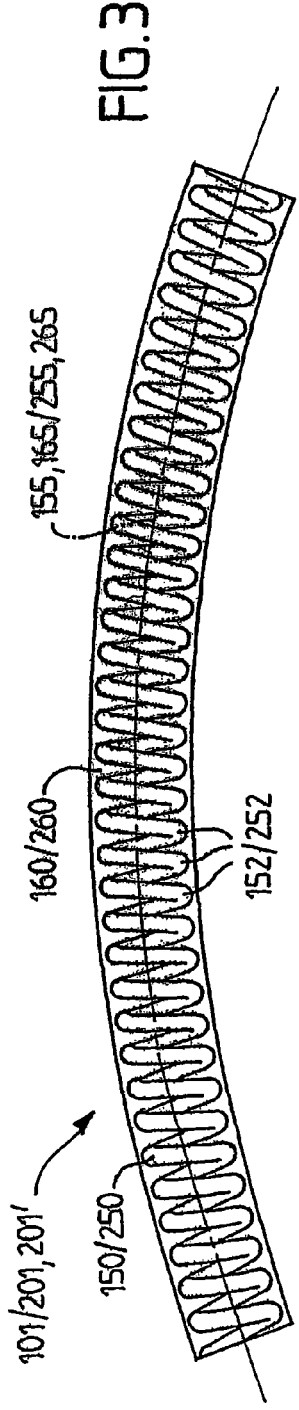
FIG. 3 shows a front view of a first embodiment of the linking element according to the invention, curved.

It should be noted that the rod (170, 270), the helical spring (150, 250) and, consequently, the linking element (101, 201, 201') can be curved, according to a desired curvature, as is illustrated in FIGS. 3, 6 and 9, in order to permit adaptation of the linking element (101, 201, 201') to a particular configuration.

The structure of the linking element (101, 201, 201') according to the invention permits compression and distraction directly on the implanted connecting assemblies, in order to permit dynamic stabilization.

The dynamic linking element according to the invention can also be combined, in the same fixation system, with rigid linking elements whose aim is to permit osteosynthesis between the implants thus linked.

The linking element (101, 201, 201') according to the invention can thus also comprise a stiffening element (143, 143'), straight or curved, in order to permit stiffening between at least two implantable connecting assemblies and thus permit osteosynthesis between the implants thus linked (FIGS. 15 through 18).

This stiffening element (143, 143') is composed, for example, of a sheet of material having a substantially U-shaped cross section, and this shape can be introduced into the receiving means of the connecting assemblies and is fixed by the fixation means of the linking element on the implantable connecting assembly.

Figure 19:
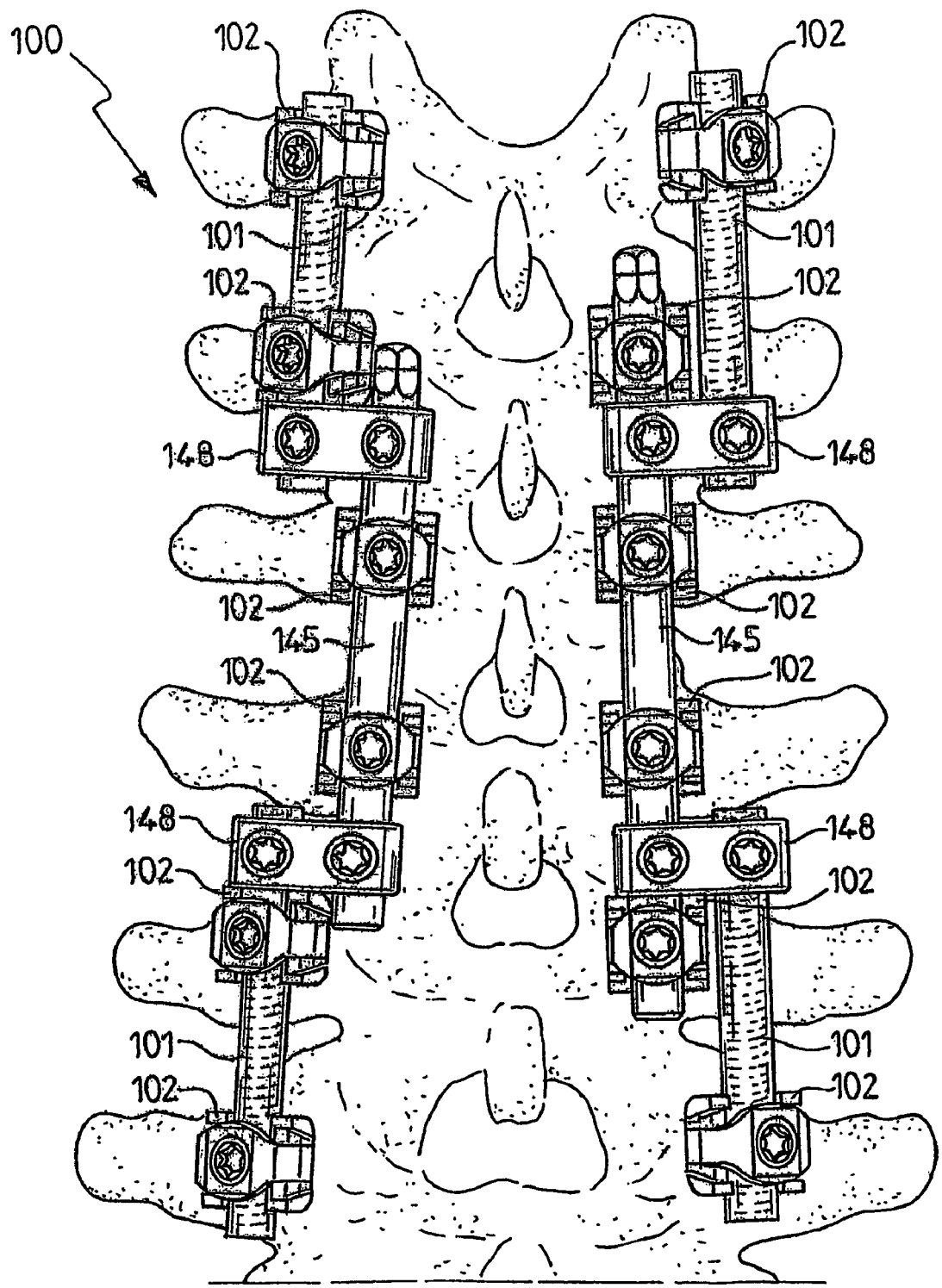
FIG. 19 shows a top view of a fixation system comprising twelve connecting assemblies according to the first embodiment, four straight linking elements according to the invention, two rigid linking elements and four domino blocks, in order to link six vertebrae to one another.
Figure 23:
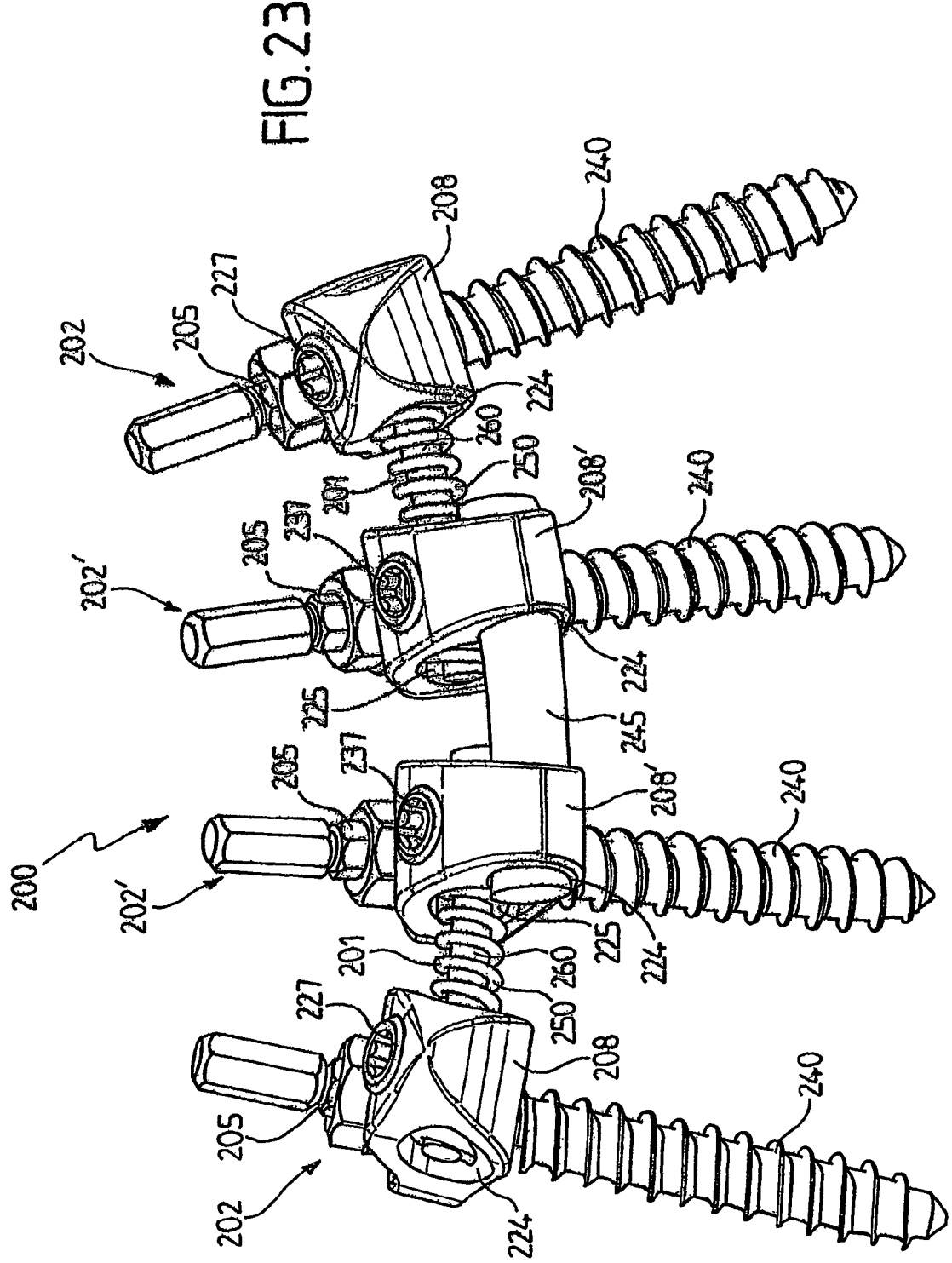
FIG. 23 shows a front view of a fixation system comprising two connecting assemblies according to the second embodiment, two connecting assemblies according to the third embodiment, two curved linking elements according to the invention, and a rigid linking element.

In place of the stiffening element (143, 143') associated with the linking element (101, 201, 201'), it is possible to position a linking element (145, 245) formed by a straight or curved rigid rod (FIGS. 19 and 23).

In the examples shown, the spring (150, 250) is made in one piece, and the helical shape is identical along the whole length of the spring.

However, it is possible to imagine the spring being interrupted inside the linking element, either by a rod, for example of parallel axis with the rest of the linking element, or by the material from which the support (160, 260) is made.

It is also possible to imagine the pitch of the helical shape changing instead of being constant.

It can additionally be imagined that the helical shape is not circular, but oblong, that the material forming the spring does not have a circular cross section, but an oblong one, or more simply that the cross-sectional shape of the support is not circular, but oblong, in order to achieve greater strength along the principal length. The receiving means for the linking element on the implant would then be consequently modified.

Figure 10:
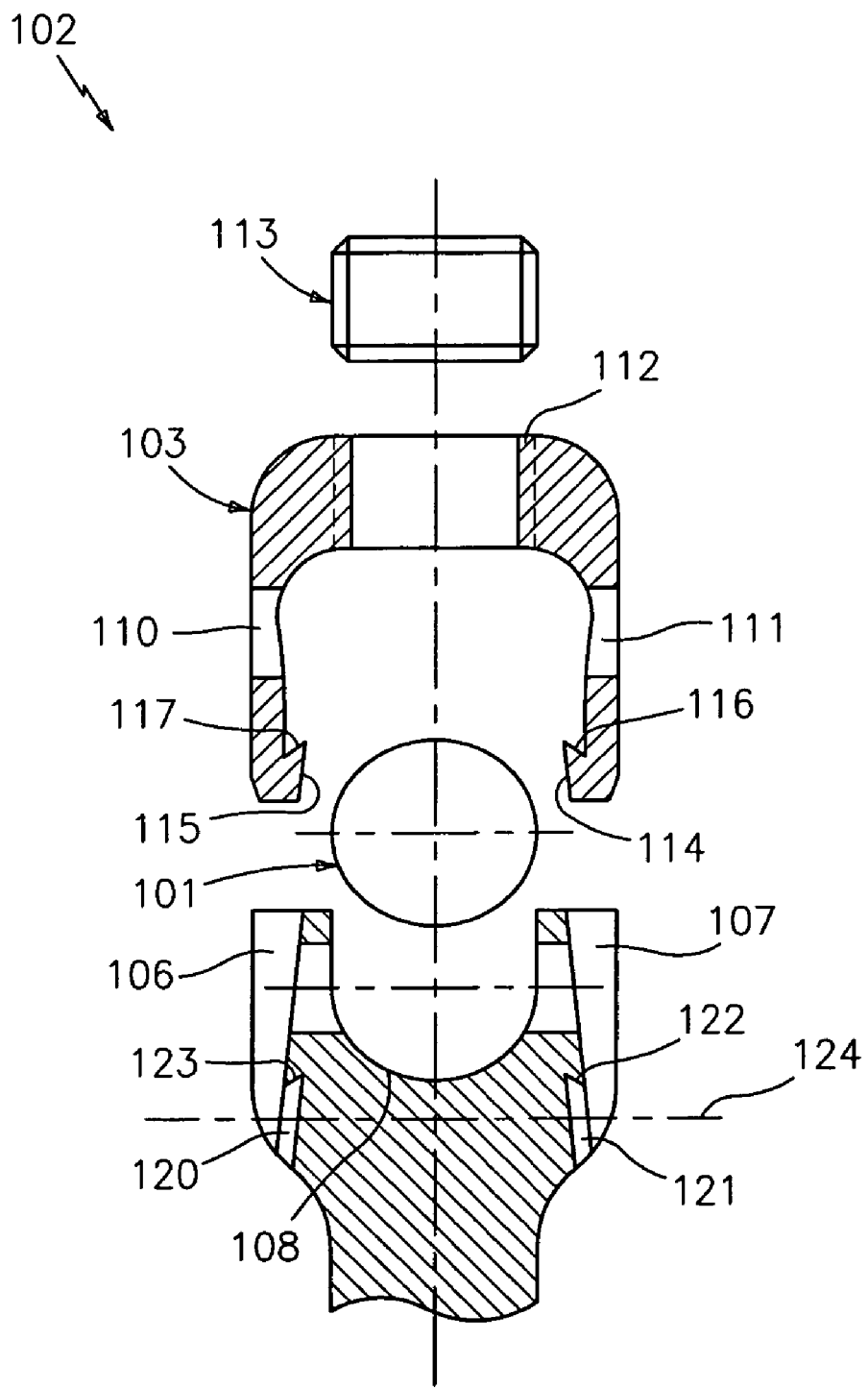
FIG. 10 shows an exploded cross-sectional view of a first embodiment of a connecting assembly for a linking element according to the invention.

Linking Element According to the Invention Used with a Connecting Assembly According to the First Embodiment According to the first embodiment, shown in FIGS. 10 through 18, the fixation system comprises a linking element (101), an implant (102) with a complementary closure piece (103), and a locking screw (113), as is shown in FIG. 10.

The implant (102) has a fork-shaped head (105) with two lateral arms (106, 107) delimiting a space intended to receive the linking element (101).

The bottom (108) of the fork has, in cross section, the general form of a horseshoe, with a concave curvature in the transverse plane corresponding to the plane in FIG. 10, and a convex curvature in the complementary plane.

The radius of concave curvature corresponds substantially to the external radius of the linking element (101). The latter thus makes contact along a semi-peripheral line. This contact by a line, rather than by an annular surface, permits a degree of freedom in pivoting and at the same time ensures more effective locking after tightening than in the case of a simple point contact.

The closure piece (103) has a general U-shape with two arms (110, 111), and the bottom of the U has an internal thread (112) for receiving a locking screw (113).

The arms (110, 111) are at a distance permitting engagement on the head. At their lower end, the arms (110, 111) have arc-shaped shoulders (114, 115) with an inclined upper surface (116, 117).

These arc-shaped shoulders (114, 115) cooperate with complementary guide means (120, 121) provided on the head (105). These guide means also have an arc-shaped and inclined contact surface (122, 123) and cooperate with the complementary contact surfaces (114, 115) when the closure piece is engaged on the head (105). They then provide guiding so as to permit pivoting of the closure piece on a transverse axis (124) and they ensure locking of the closure piece (103) on the head (105), and thus locking of the linking element (101) after the screw (113) is tightened.

Figure 11:
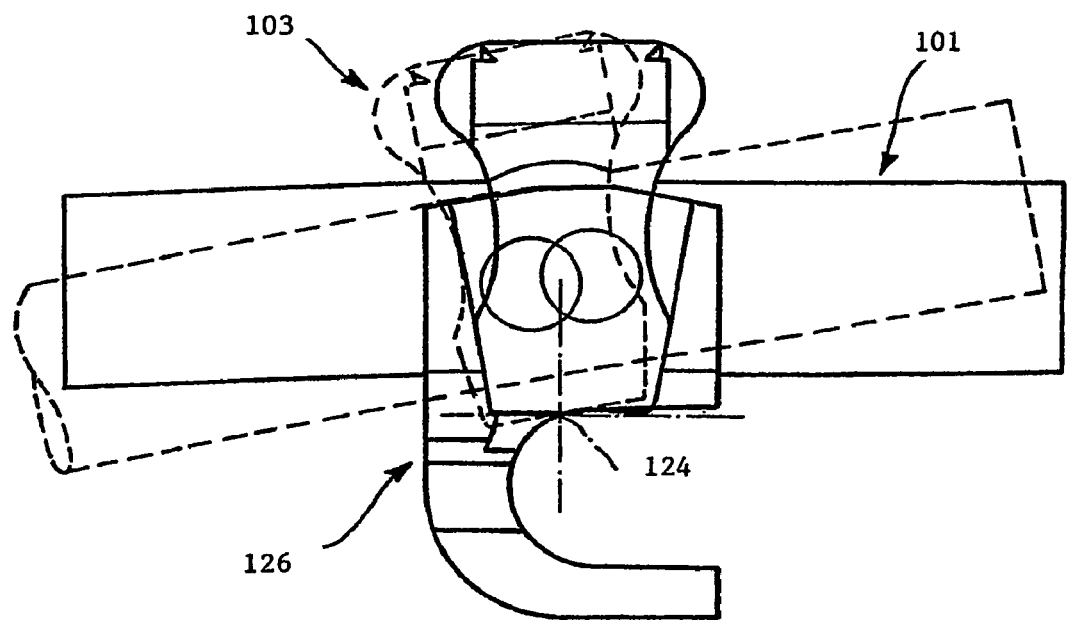
FIG. 11 shows a front view of the connecting assembly from FIG. 10, when mounted.

FIG. 11 is a side view showing that the linking element 101 has a degree of freedom in terms of tilting about a transverse axis (124). This permits independence of the implant and makes it possible to position the implant by means of a hook (126) on the pedicle, and to independently seek the best orientation of the linking element 101 without interference between these two constraints. The horseshoe shape and the mobility of the closure piece makes it possible to adapt the locking and to avoid unwanted rotation or displacement of the rod during tightening of the screw (113).

The hook (126) delimits a U-shaped space (127) for connection to the lamina of a vertebra. To ensure a temporary hold, an elastic leaf (128) is arranged inside this U-shaped space and provides for a temporary hold on the bone in such a way that the blade of the hook does not risk interfering with the marrow or other structure.

The elastic leaf (128) pushes the hook back in a posterior direction relative to the patient and avoids lesions of the vital tissues during the phase of correction by rotation of the rod.

Figure 12:
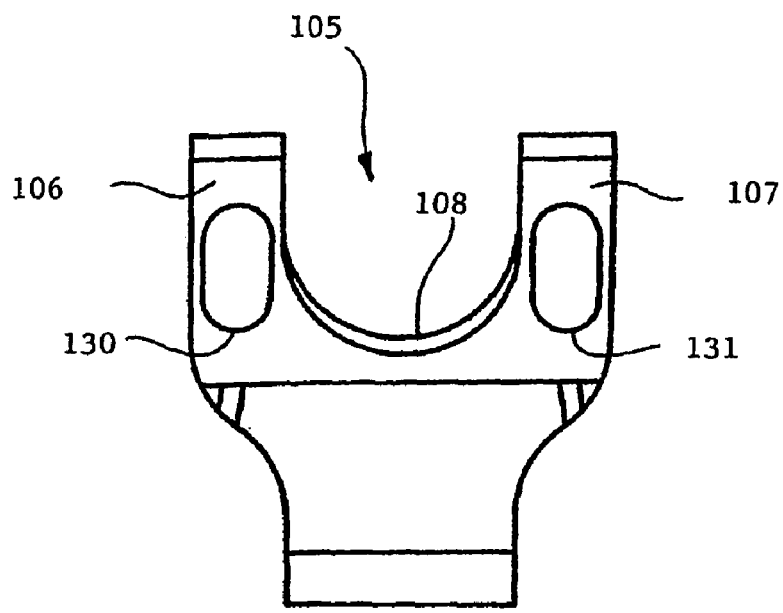
FIG. 12 shows a side view of the receiving means of the connecting assembly from FIG. 10.
Figure 13:
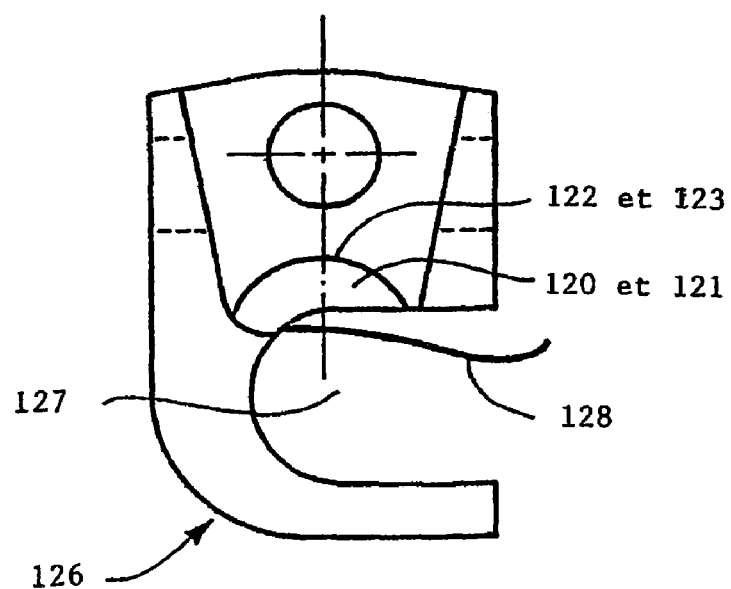
FIG. 13 shows a front view of the receiving means of the connecting assembly from FIG. 10.

FIGS. 12 and 13 show side views of the implant, without the closure piece.

The implant has two slots (130, 131) permitting passage of an instrument with two jaws which fit in the slots (130, 131), and an element which exerts a force on the linking element (101) to effect its lateral and/or vertical displacement, so as to permit positioning of the rod in the fork by way of the closure piece (103).

FIGS. 11 through 13 show an implant whose means for anchoring in the bone are composed of a hook (126); however, the anchoring means can also be composed of a bone screw (140), as is shown in FIGS. 14 through 18.

Figure 14:
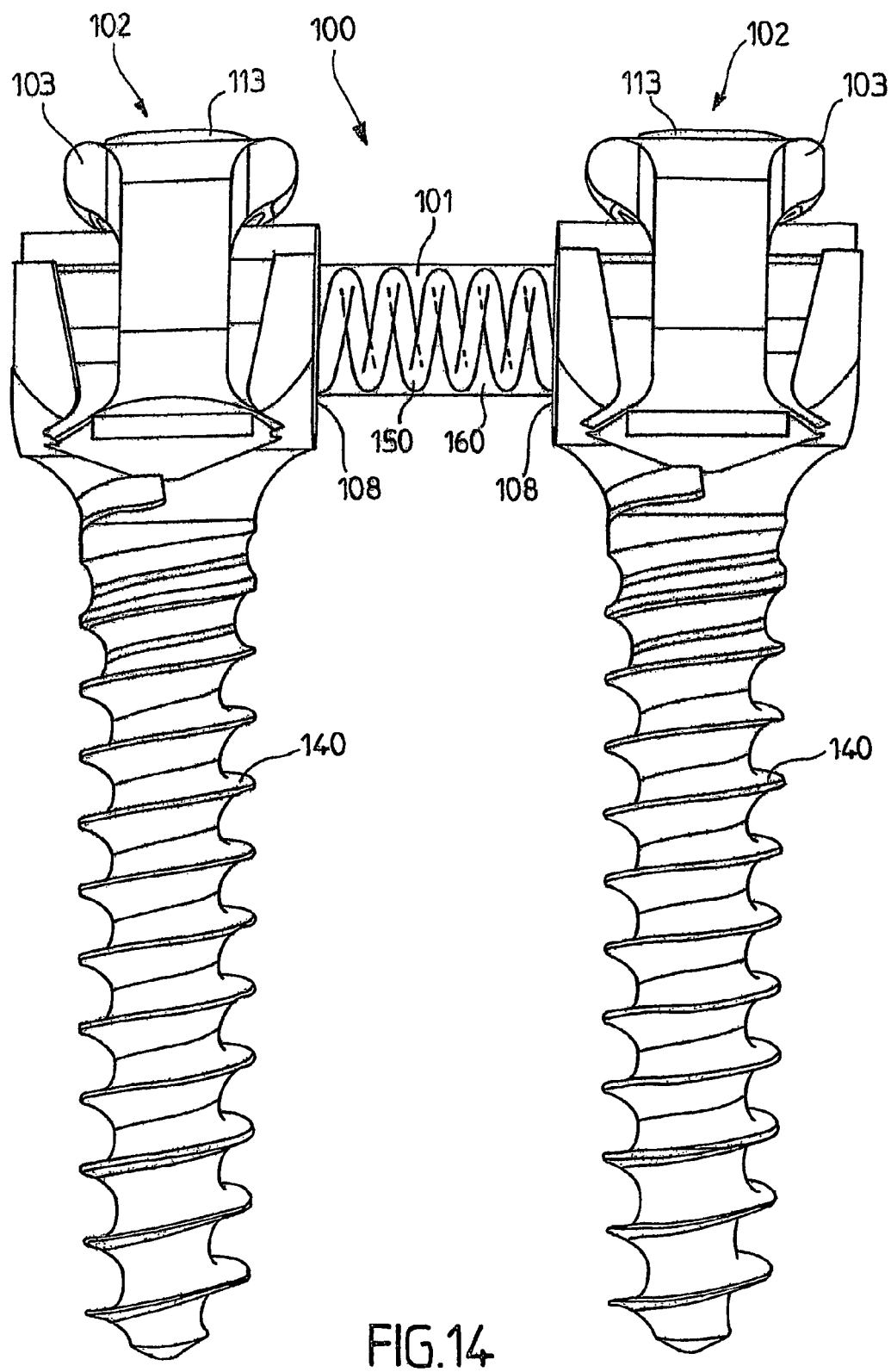
FIG. 14 shows a front view of a fixation system comprising two connecting assemblies according to the first embodiment, and a straight linking element according to the invention.

FIG. 14 shows the configuration of a fixation system (100) with two implants/connecting assemblies (102) according to the first embodiment, and a straight linking element (101) according to the invention.

The linking element (101) is arranged in the bottom (108) of each of the connecting assemblies (102), and the closure piece (103) closes the means for receiving the linking element. A screw (113) firmly locks the linking element (101) in the desired position on each connecting assembly (102).

In FIG. 14, the linking element (101) is composed of a spring (150) embedded in the support (160); however, all the embodiments of the linking element (101) that have been discussed above are conceivable for linking the two connecting assemblies (102).

Figure 15:
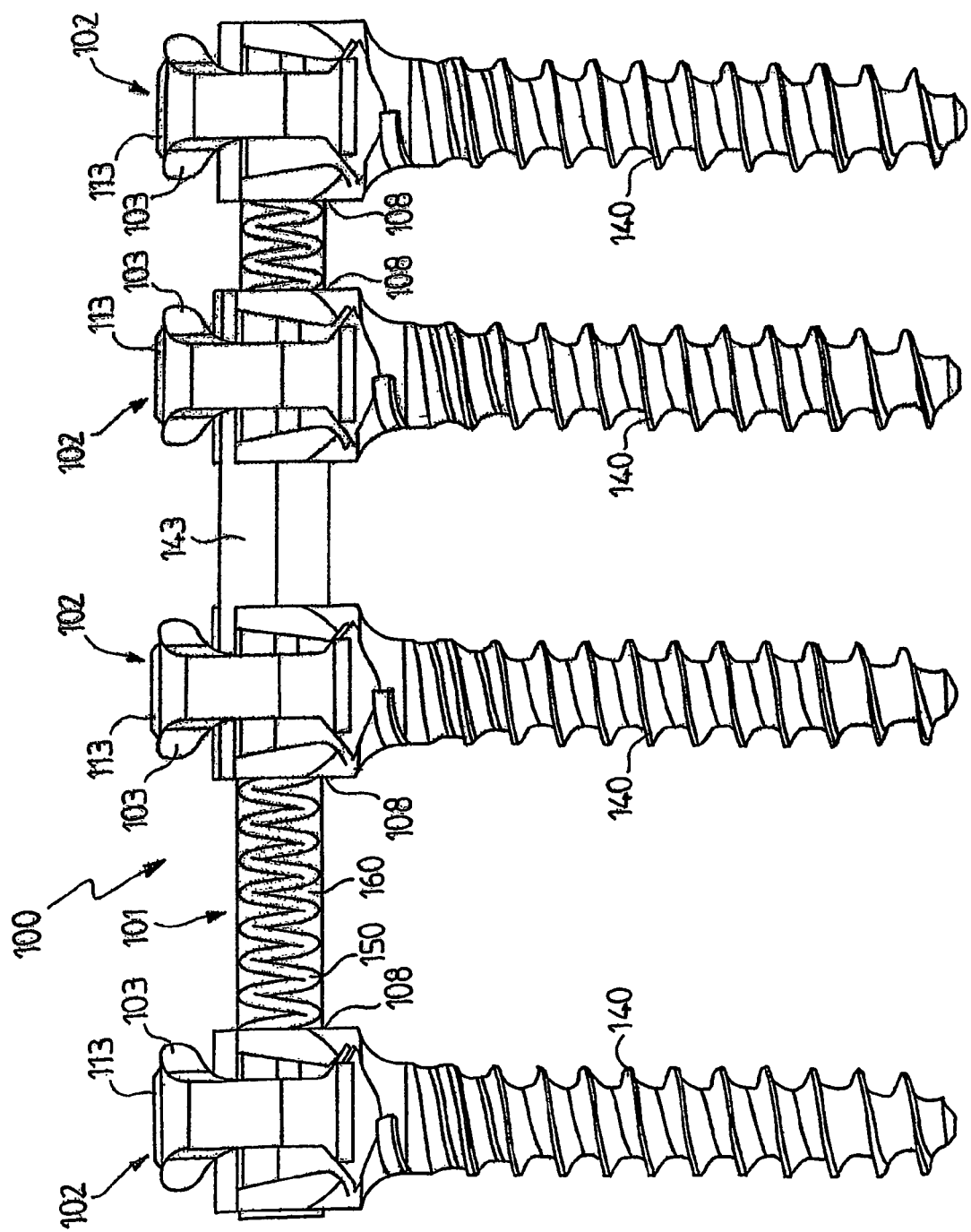
FIG. 15 shows a front view of a spinal fixation system comprising four connecting assemblies according to the first embodiment, and a straight linking element according to the invention, stiffened along a straight portion.
Figure 16:
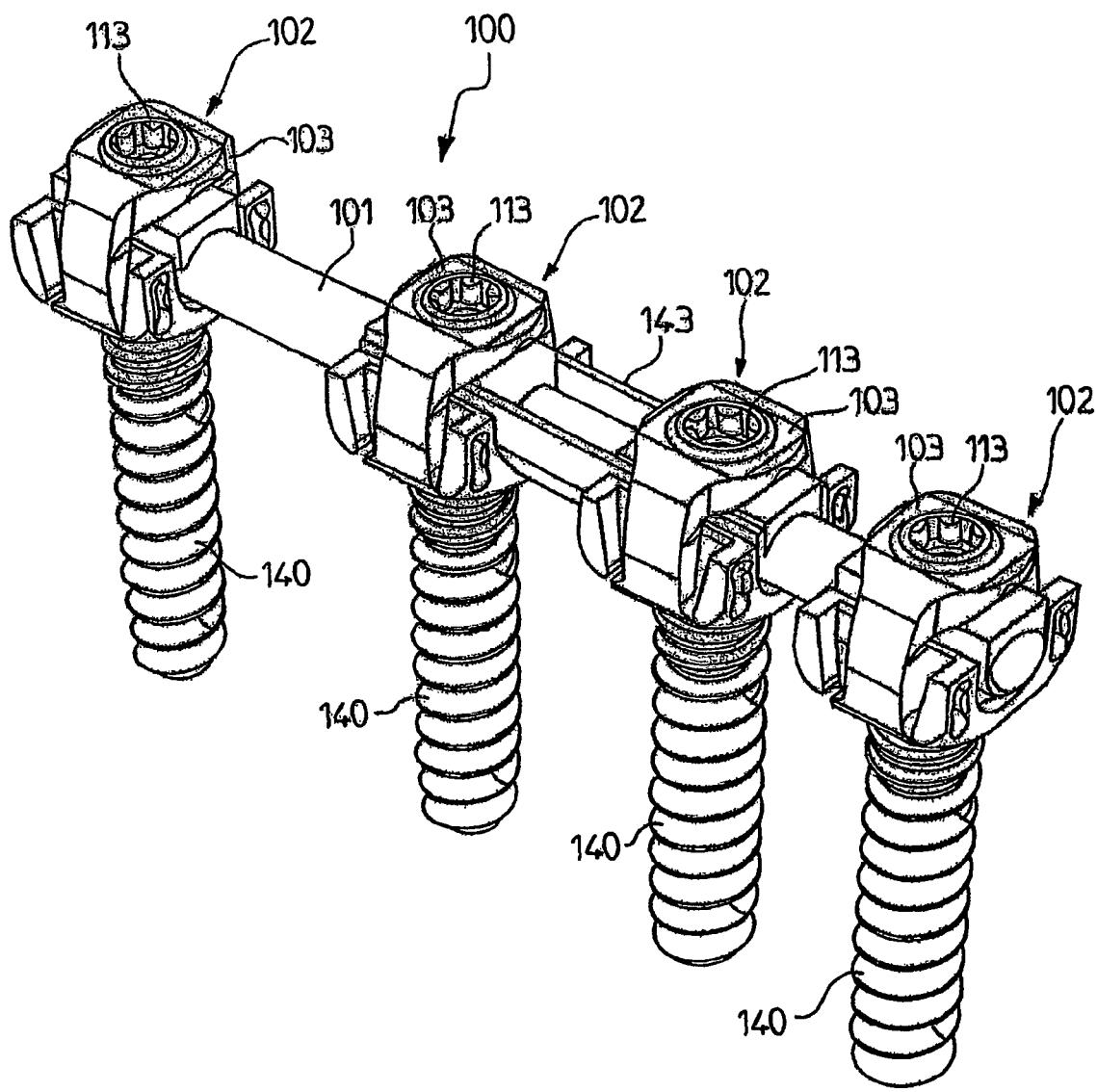
FIG. 16 shows a perspective view of FIG. 15.

FIGS. 15 and 16 show the configuration of a fixation system (100) with four implants/connecting assemblies (102) according to the first embodiment, and a single and straight linking element (101) according to the invention.

The linking element (101) is arranged in the bottom (108) of each of the connecting assembles (102), and the closure piece (103) closes off the receiving means of the connecting assembly. A screw (113) firmly locks the linking element (101) in the desired position on each connecting assembly (102).

A straight stiffening element (143) is arranged between the two connecting assembles situated at the center of the fixation system. This stiffening element (143) is also arranged in the bottom (108) of each of the two central connecting assemblies (102). The closure piece (103) will also lock the stiffening element (143) in the receiving means of each central connecting assembly, under the linking element (101), and the screw (113) also firmly locks the stiffening element (143) in the desired position on each central connecting assembly (102), by bearing on the linking element (101) (there is no contact between the screw (113) and the stiffening element (143)).

In FIG. 15, the linking element (101) is composed of a spring (150) embedded in the support (160); however, all the embodiments of the linking element (101) that have been discussed above are conceivable for linking the two connecting assemblies (102). In FIG. 16, the internal constitution of the linking element (101) is not shown, in order not to needlessly complicate the drawing.

Figure 17:
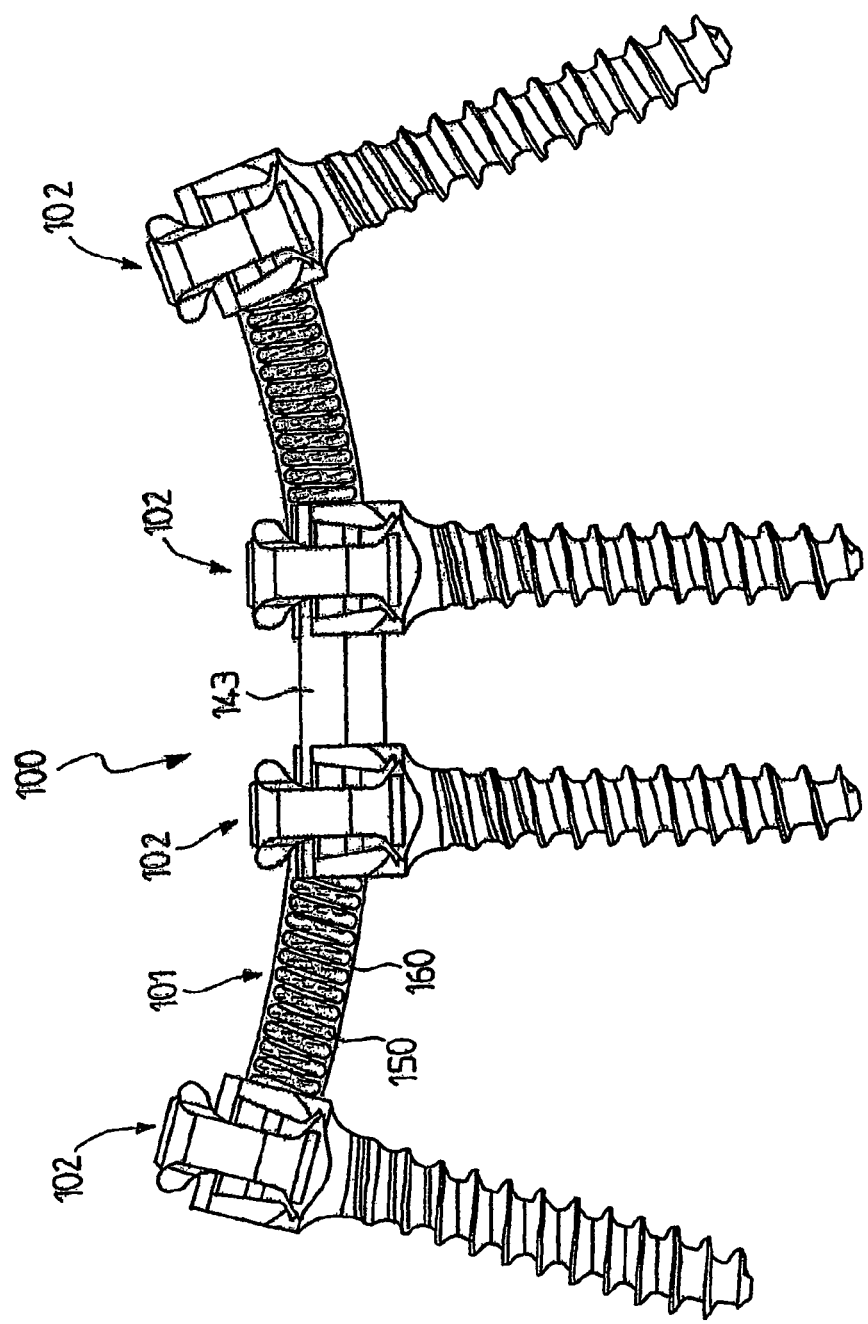
FIG. 17 shows a front view of a fixation system comprising four connecting assemblies according to the first embodiment, and a curved linking element according to the invention, stiffened along a straight portion.

FIG. 17 shows the configuration of a fixation system (100) with four implants/connecting assemblies (102) according to the first embodiment, and a single and curved linking element (101) according to the invention. However, in this embodiment, the linking element (101) is only curved between the first and second connecting assemblies and between the third and fourth connecting assemblies. A straight stiffening element (143) is arranged between the two connecting assemblies situated at the center of the fixation system.

The linking element (101) including the stiffening element (143) is arranged in the bottom (108) of each of the connecting assembles (102), and the closure piece (103) closes the receiving means of the connecting assembly. A screw (113) firmly locks the linking element (101) in the desired position on each connecting assembly (102).

In FIG. 17, the linking element (101) is composed of a spring (150) embedded in the support (160); however, all the embodiments of the linking element (101) that have been discussed above are conceivable for linking the two connecting assemblies (102).

Figure 18:
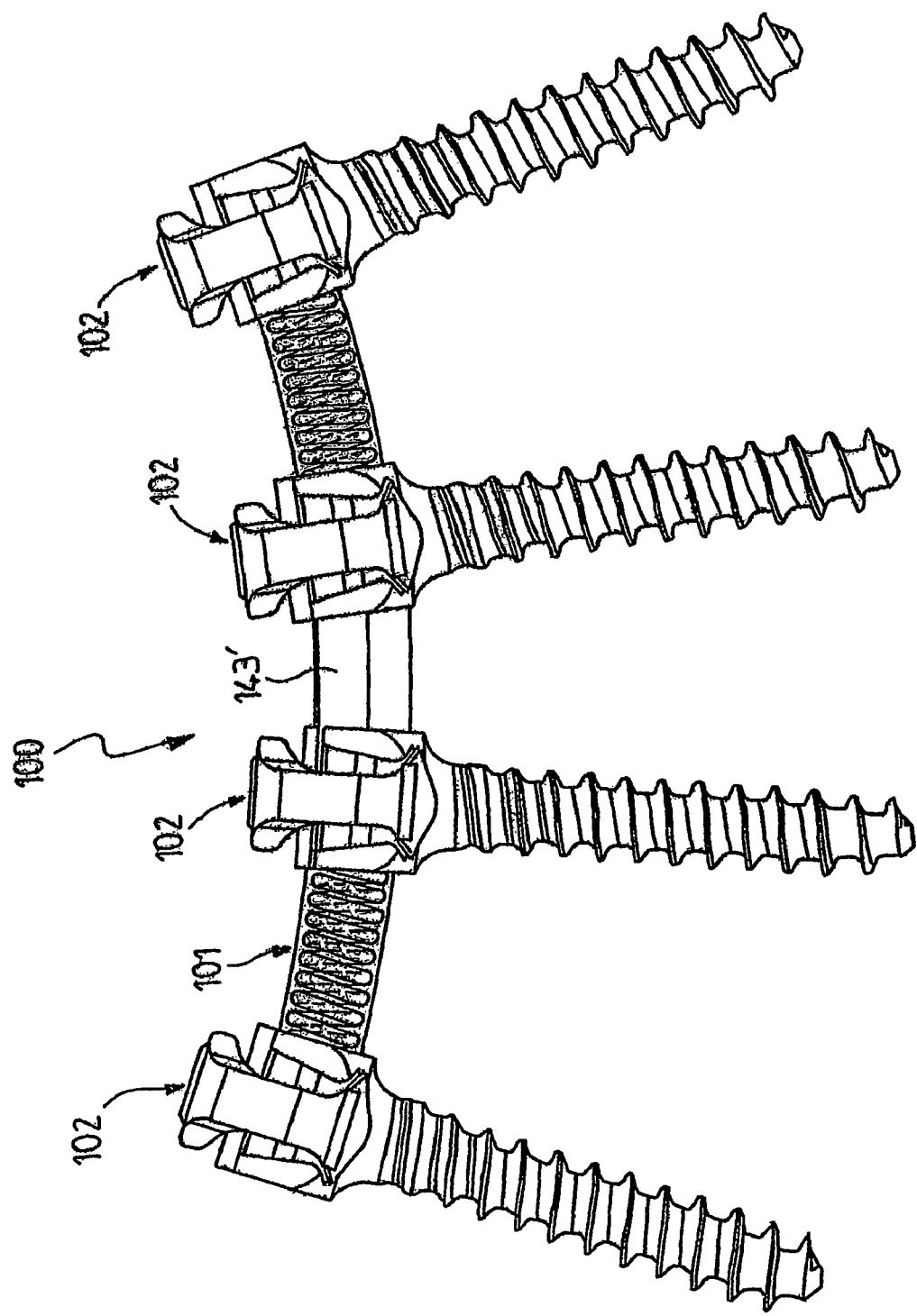
FIG. 18 shows a front view of a fixation system comprising four connecting assemblies according to the first embodiment, and a curved linking element according to the invention, stiffened along a curved portion.

FIG. 18 shows the configuration of a fixation system (100) with four implants/connecting assemblies (102) according to the first embodiment, and a single and curved linking element (101) according to the invention.

In this embodiment, the linking element (101) is curved between all the connecting assemblies (102). A curved stiffening element (143') is arranged between the two connecting assembles situated at the center of the fixation system.

The linking element (101) including the stiffening element (143') is arranged in the bottom (108) of each of the connecting assemblies (102), and the closure piece (103) closes the receiving means of the connecting assembly. A screw (113) firmly locks the linking element (101) in the desired position on each connecting assembly (102).

In FIG. 18, the linking element (101) is composed of a spring (150) embedded in the support (160); however, all the embodiments of the linking element (101) that have been discussed above are conceivable for linking the two connecting assemblies (102).

FIG. 19 shows the configuration of a fixation system (100) with twelve implants/connecting assemblies (102) according to the first embodiment, each one implanted in a pedicle of a vertebra. These twelve implants are linked to one another, in the upper part and lower part of the fixation system, by four straight linking elements (101) according to the invention and, in the central part, by two rigid linking elements (145) formed by straight rods.

The connection between the rigid linking elements (145) and the linking elements (101) according to the invention is effected with the aid of four means of connection, so-called domino blocks. Each of these means of connection has two receiving means, for receiving a linking element in each receiving means, and retention means formed by two nuts which connect fixation means to said receiving means.

As will be noted, the left-hand side shows a version of the invention in which the domino blocks (148) are situated at the end of the rigid linking element (145), this element being fixed to the central pedicles with the aid of two central implants. On the right-hand side, the domino blocks (148) are situated at the end of the linking elements (101) according to the invention, the rigid linking element (145) being fixed to the central pedicles with the aid of four implants.

In FIG. 19, the linking elements (101) are each composed of a spring (150) embedded in the support (160); however, all the embodiments of the linking element (101) that have been discussed above are conceivable for linking the connecting assemblies (102) to one another or to the domino blocks.

Figure 20:
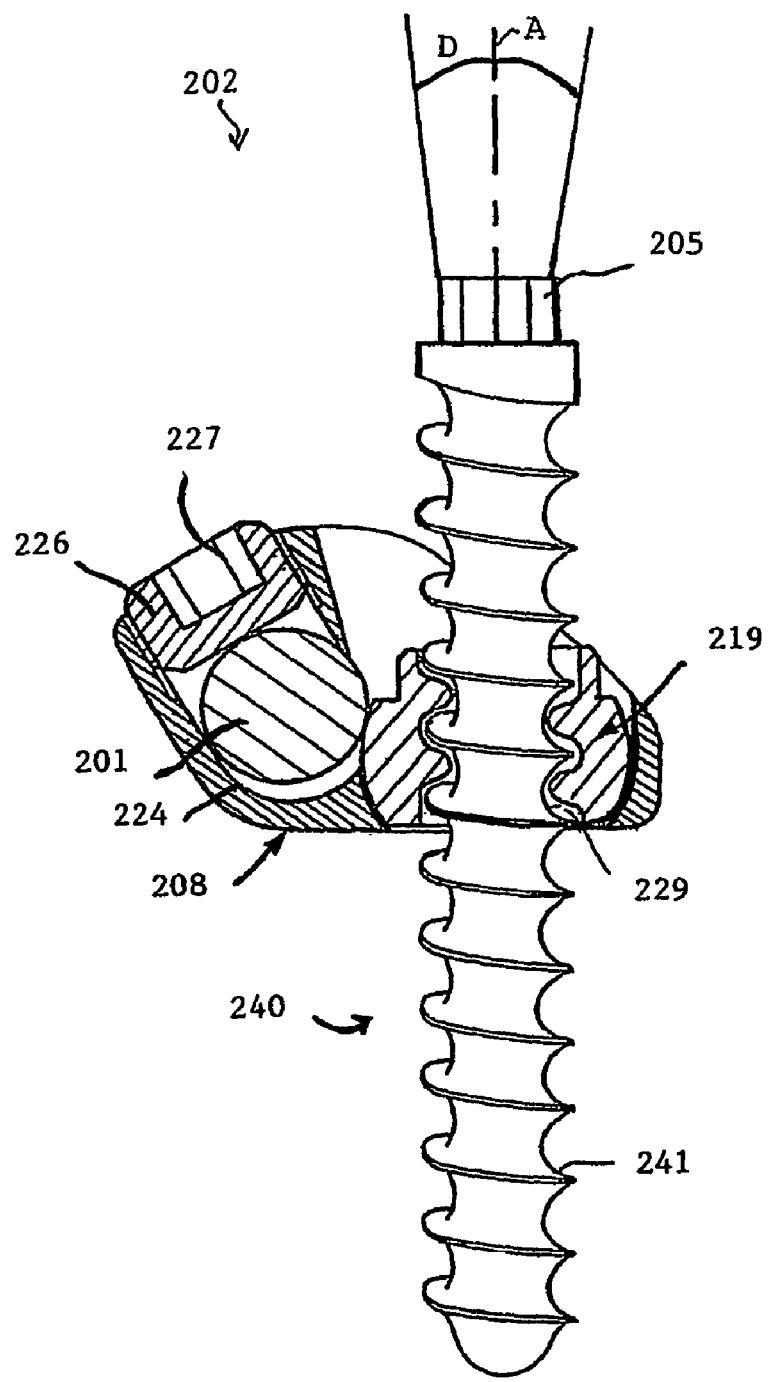
FIG. 20 shows a cross section through a second embodiment of a connecting assembly for a linking element according to the invention.

Linking Element According to the Invention Used with a Connecting Assembly According to the Second Embodiment According to the second embodiment shown in FIGS. 20 through 23, the fixation system comprises a linking element (201), an implant (202, 202') formed by a connection means and an anchoring means, the anchoring means being formed, for example, by a bone screw (240) having a thread of the bone type (241), as is shown in FIG. 20.

The bone-type thread (241) has a main function: that of ensuring anchoring in the bone. It may also have a secondary function: that of receiving the connection system for a linking element when the connection zone (229) coincides with the upper part of the bone thread (241).

At the upper end of the screw (240), a system (205) for driving it in rotation is provided. This system, for example a hexagon, has two functions: on the one hand it allows the screw (240) to be driven in rotation as the latter is penetrating the bone, and, on the other hand, it also has the role of blocking rotation during final tightening of the mechanism, in order to avoid excessive penetration of the screw (240) into the bone.

The connection means allows a longitudinal abutment to be formed along the screw (240) by means of a connector (208, 208').

The connection means can comprise a nut (219). In this case, the internal thread (207) of the nut (219) corresponds to the threading of the connection zone (229); that is to say, in the version shown in FIGS. 20 through 23, to the bone thread (241) of the screw (240). The nut (219) is screwed onto the part of the screw not buried in the bone.

The nut (219) has a spherical shape (220) at its lower part. This spherical shape is intended to permit free positioning of the nut (219) on the connector (208) where there is a seat of the same type, or on the linking element (201). This spherical shape (220) also serves as a longitudinal positioning abutment with the connector (208) or with the linking element (201). In the preferred application, the connection means is flanged in the connector (208) or in the linking element (201) in such a way as to secure the two parts while permitting rotation of the connection means on the connector (208) or on the linking element (201).

A drive system (221), for example an external hexagon, is also provided on the connection means above its spherical part (220), in such a way as to be able to adjust its height and also adjust the connector (208) or the linking element (201) along the screw (240). As a consequence of the possibility of rotation of the connector on the connection means, a cone (222) of entry into the connector (208) is provided for the passage of the ancillary for driving the connection means in rotation. By way of example, the angular clearance D of the axis A of the connector on the connection means is preferably 30° when the ancillary for driving the connection means in rotation is in place, as is illustrated in FIG. 20.

Figure 22:
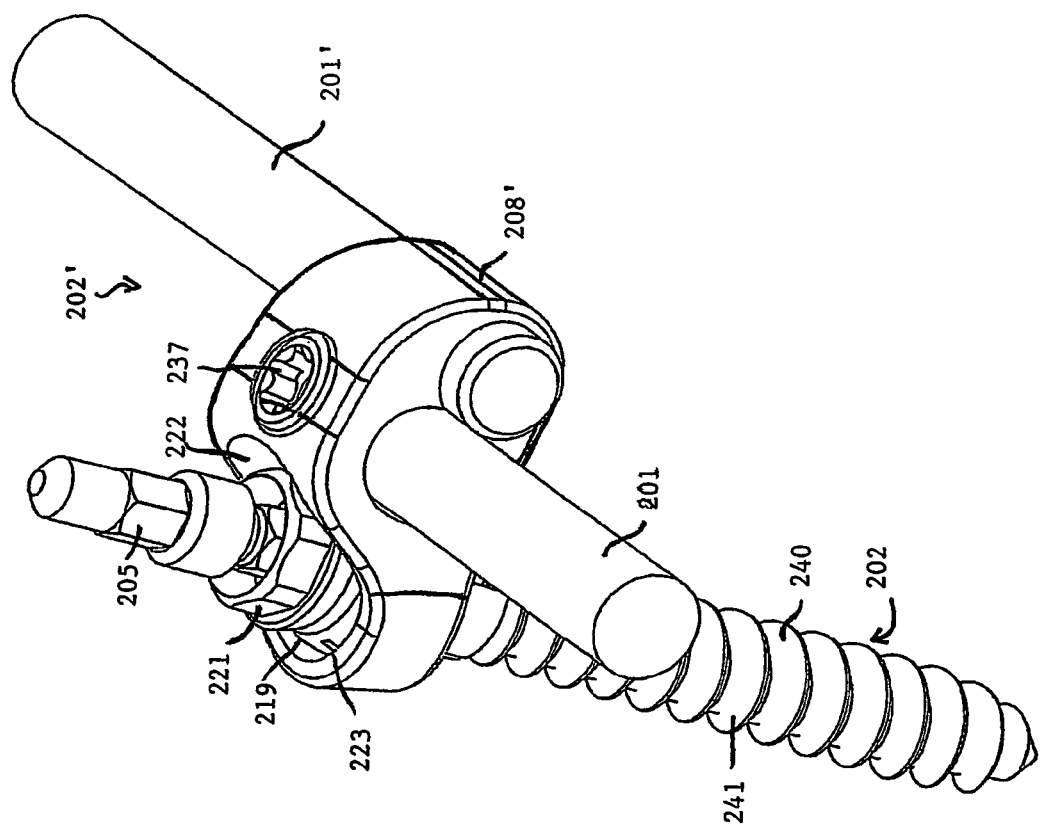
FIG. 22 shows a perspective view of FIG. 21.

Slits (223), visible in FIG. 22, are machined in the spherical part of the connection means in such a way as to create a deformation upon final tightening of the system. The aim of this deformation is to lock the screw (226) in rotation.

The slits (223) can be positioned transversely or longitudinally.

The longitudinal slits preferably open out in the lower part of the spherical shape (220). There can be one, two, three, four, five or more of them.

Figure 21:
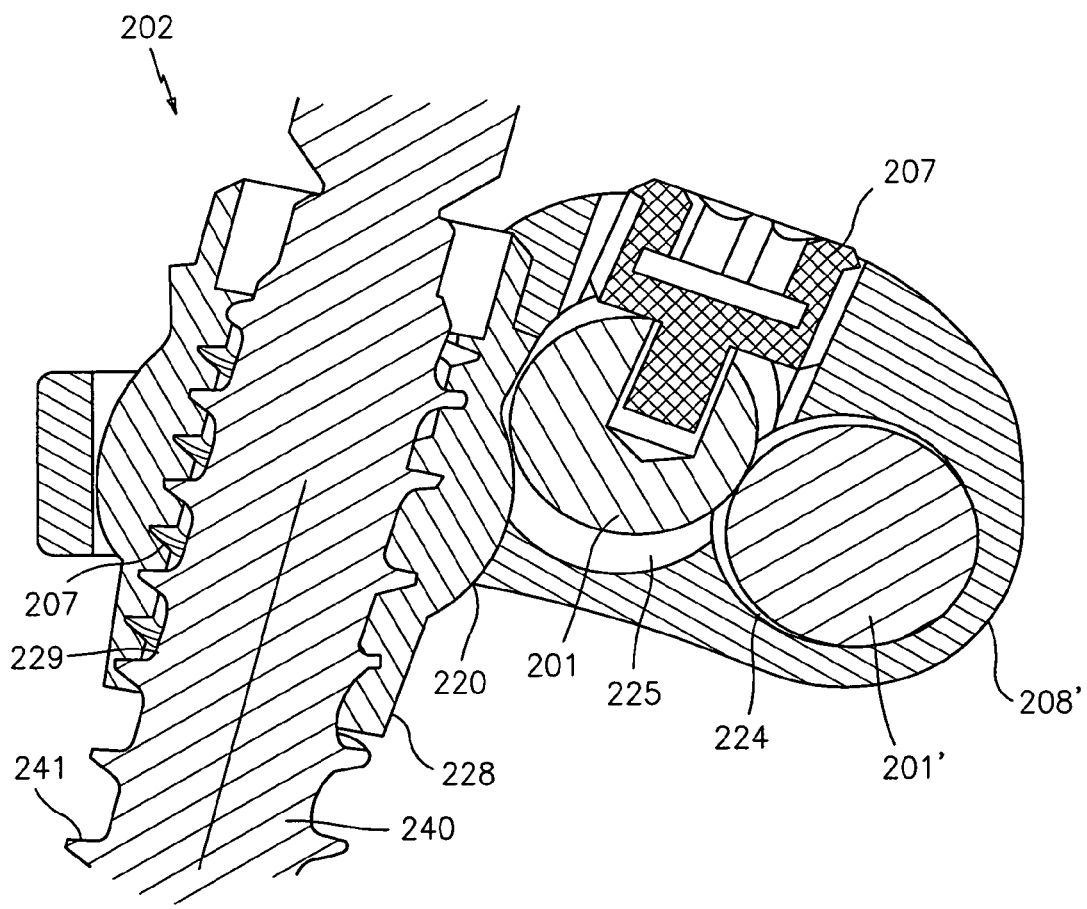
FIG. 21 shows a partial cross section through a third embodiment of a connecting assembly for a linking element according to the invention.

In its lower part, the connection means comprises a skirt (228), visible in FIG. 21. This skirt (228) permits a mechanical transition between the screw (240) and the spherical shape (220). This is because too sharp a transition would promote rupturing of the screw at the base of the spherical shape (220) in the event of dynamic forces. The skirt (228) thus permits a better distribution of the stress occurring on engagement of the screw in the nut.

This skirt (228) can be threaded at its end in order to make its penetration into the bone easier.

The connection zone (229) of the screw (240) can be formed in the upper part of the bone thread and can have a thread identical to the bone thread, as shown, although it can also have a different thread, or it may not be threaded.

In the latter case, the connection means consequently has a smooth inside wall and does not constitute a nut.

In the basic version of the second embodiment, illustrated in FIG. 20, the connector (208) is provided with a single seat (224) for receiving a linking element (201). This seat (224) can be of oblong shape in the case of a connector (208) of the closed type, or in the shape of a U, open on one of its faces, in the case of a connector of the open type. In the case of a connector (208) of the closed type, the linking element (201) must be threaded into it, whereas, in the case of an open connector, the linking element (201) can be introduced posteriorly or laterally on the connector.

The seat (224) for receiving the linking element (201) is provided in such a way that the linking element (201) can bear on the spherical shape (220) of the nut (219), as is illustrated in FIG. 20.

It will therefore be appreciated that, before final fixation, the linking element (201) is free relative to the screw (226) in three axes of rotation and in two directions of translation:

Rotation of the connector (208) and thus of the linking element (201) about the connection means in two axes perpendicular to the screw (240);

Rotation of the connector (208) and thus of the linking element (201) about the connection means in an axis identical to that of the screw (240);

Translation of the linking element (201) in the connector (208) along the axis thereof;

Translation of the connector (208) and thus of the linking element (201) along the screw (240) by virtue of the possibility of adjustment of the connection means.

In addition, the rotation of the linking element (201) about itself can give a supplementary degree of freedom to the connecting assembly (202).

The connector (208) also has a locking system. In the basic version illustrated in FIG. 20, this locking system is a nut (226) provided with a drive system (227) for applying a torque sufficient for good mechanical stability of the assembly.

Such a connection piece is locked by means of the pressure of the linking element (201) on the spherical shape (220). With the linking element (201) being made secure to the connector (208) by the pressure exerted by the nut (226), the degrees of freedom are then all set.

In a more complex version of the second embodiment, shown in FIGS. 21 and 22, the connecting assembly (202') can receive two linking elements (201, 201').

The connector (208') comprises a locking seat (225) in which one linking element (201) can be introduced, the other linking element (201') being introduced into the seat (224).

The locking seat (225) opens out in a substantially perpendicular direction for introduction of a plug (237), as is shown in FIG. 20.

In this version, the assembly is tightened by the force exerted on the linking element (201') and, at the same time, on the spherical part (220) by the linking element (201).

It is necessary to provide a plurality of connectors in order to be able to choose the one in which the distance between the screw and the linking element or linking elements is suitable.

FIG. 23 shows the configuration of a fixation system (200) with two implants/connecting assemblies (202) according to the basic version of the second embodiment at the ends, and with two implants/connecting assemblies (202') according to the more complex version of the second embodiment at the center.

A curved linking element (201) according to the invention is arranged between the first and second connecting assemblies, and another curved linking element (201) according to the invention is arranged between the third and fourth connecting assemblies. A curved and rigid linking element (245) is arranged between the two connecting assemblies situated at the center of the fixation system.

In the connecting assemblies (202), the linking elements (201) are arranged respectively in the seats (224) of the connectors (208).

In the connecting assemblies (202'), the linking elements (201) are arranged respectively in the locking seats (225) of the connectors (208'), and the linking element (245) is arranged respectively in the seats (224) of the connectors (208').

In FIG. 23, the curved linking elements (201) are in each case composed of a spring (250) and of a support (260), of the type shown in FIG. 6; however, all the embodiments of the linking element (201) that have been discussed above are conceivable for linking the connecting assemblies (202, 202').

The invention has been described above by way of a non-limiting example. It will be appreciated that the person skilled in the art may form different configurations, especially by replacing the hook by a pedicle screw, or a vertebral screw for placement on the anterolateral face of the spine.

The invention claimed is:

1. A linking element for a spinal fixation system designed to link at least two implantable connecting assemblies, wherein said element is capable of being deformed from a linear state to a curved state and comprises at least partly of a support made of a flexible polymer material which allows said support to be curved, a rod substantially coaxial with said support, a spring being formed of a plurality of turns surrounding the rod, said support being cylindrical or tubular in shape and having an inner diameter, said turns having an inner diameter which forms a cylindrical space in which said rod is positioned and an external diameter which is greater than said inner diameter of said support resulting in said turns being at least partly embedded in the polymer material of said support.

2. The linking element according to claim 1, wherein the spring is a helical spring having an axis substantially parallel with an axis of said support.

3. The linking element as claimed in claim 2, wherein said rod is substantially coaxial with said spring.

4. The linking element as claimed in claim 2, wherein said rod has an external diameter smaller than the internal diameter of said turns.

5. The linking element as claimed in claim 1, wherein said element further comprises a straight or curved stiffening element.

6. The linking element as claimed in claim 5, wherein said stiffening element is composed of a sheet of material with a substantially U-shaped cross section.

7. The linking element as claimed in claim 1, wherein said rod is curved.

8. The linking element as claimed in claim 1, wherein said rod is straight.

9. The linking element as claimed in claim 1, wherein said rod is at least coextensive with said support, and said spring is at least coextensive with said support.

10. A spinal fixation system comprising at least two implantable connecting assemblies linked by at least one linking element, said at least one linking element being capable of being deformed from a linear state to a curved state and comprising at least partly of a support made of a flexible polymer material which allows said support to be curved, a rod substantially coaxial with said support, a spring being formed of a plurality of turns surrounding rod, said support being cylindrical or tubular in shape and having an inner diameter, said turns having an inner diameter which forms a cylindrical space in which said rod is positioned and an external diameter which is greater than said inner diameter of said support resulting in said turns being at least partly enclosed in said polymer material of said support.

11. The spinal fixation system as claimed in claim 10, further comprising a stiffening element fixed at least to the two implantable connecting assemblies.

12. The spinal fixation system as claimed in claim 10, further comprising at least one rigid linking element.

13. The spinal fixation system as claimed in claim 10, wherein each said implantable connecting assembly has a fork shaped head with two lateral arms delimiting a space for receiving a respective linking element and a closure piece with a U-shape, two arms, and an internal thread for receiving a locking screw.

14. The spinal fixation system as claimed in claim 13, wherein said lateral arms of said fork shaped head have arc shaped shoulders with an inclined upper surface and said closure piece has complementary guide means for cooperating with said arc shaped shoulders when the closure piece is engaged on said head.

15. The spinal fixation system as claimed in claim 10, wherein said rod is at least coextensive with said support and said spring is at least coextensive with said support.

* * * * *